United States Patent
Hubbard et al.

(10) Patent No.: US 6,905,657 B2
(45) Date of Patent: Jun. 14, 2005

(54) METHODS AND DEVICES FOR STORING AND DISPENSING LIQUIDS

(75) Inventors: Allyn Hubbard, Medfield, MA (US); Samesh Kale, Alliston, MA (US); Scott Rollins, Oxford, CT (US); Jeremy P. Springhorn, Guilford, CT (US); Stephen P. Squinto, Bethany, CT (US); Prasad R. Akkapeddi, Fairfax, VA (US)

(73) Assignee: BioProcessors Corp., Woburn, MA (US)

( * ) Notice: Subject to any disclaimer, the term of this patent is extended or adjusted under 35 U.S.C. 154(b) by 387 days.

(21) Appl. No.: 09/827,570

(22) Filed: Apr. 5, 2001

(65) Prior Publication Data

US 2002/0025582 A1 Feb. 28, 2002

Related U.S. Application Data

(60) Provisional application No. 60/194,586, filed on Apr. 5, 2000.

(51) Int. Cl.[7] .............................. B01L 3/02; G01N 1/10; B65B 1/04
(52) U.S. Cl. ....................... 422/100; 422/920; 422/924; 422/99; 436/180; 141/318; 73/863.32; 73/864; 73/864.01; 73/864.11; 73/864.14; 73/864.34
(58) Field of Search ................................. 422/100, 920, 422/924; 436/180; 73/863.32, 864, 864.01, 864.11, 864.14, 864.34, 427; 141/318

(56) References Cited

U.S. PATENT DOCUMENTS

| | | | |
|---|---|---|---|
| 4,444,062 A | * | 4/1984 | Bennett et al. .......... 73/863.32 |
| 5,658,802 A | | 8/1997 | Hayes et al. |
| 5,741,554 A | | 4/1998 | Tisone ........................ 427/424 |
| 5,872,010 A | | 2/1999 | Karger et al. ............... 436/173 |
| 5,927,547 A | | 7/1999 | Papen et al. ................... 222/57 |

(Continued)

FOREIGN PATENT DOCUMENTS

| | | |
|---|---|---|
| DE | 197 37 173 A | 3/1999 |
| EP | 0 434 149 A | 6/1991 |

(Continued)

OTHER PUBLICATIONS

PCT International Search Report.
Onnerfjord et al., Picoliter Sample Preparation in MALDI–TOF MS Using a Micromachined Silicon Flow–Through Dispensor, Anal. Chem. 70:4755, 1998.

(Continued)

*Primary Examiner*—Jan Ludlow
*Assistant Examiner*—B. R. Gordon
(74) *Attorney, Agent, or Firm*—Wolf, Greenfield & Sacks, P.C.

(57) ABSTRACT

In a liquid handling system including a liquid handling substrate having a plurality of channels for conducting a liquid sample in said substrate, where the channels terminate in a plurality of exit ports in an outer surface of the substrate for transfer of a quantity of the liquid sample. The handling system also includes a liquid storage and dispensing substrate having a plurality of separable cartridges corresponding to the channels, with each cartridge terminating at a microelectro mechanical system (MEMS) comprising a laminate of glass, silicon and a piezoelectric substance. The handling system further includes a liquid detecting system comprising a light emitting diode and a photo-detector, where each channel includes a reservoir in communication with a corresponding cartridge creating an interface therebetween. The handling system enables a method for storing and dispensing liquids including drawing a liquid sample into the channels either by capillary action, vacuum, electrostatic flow, a minipump or any combination thereof, storing the liquid sample into the cartridge, and dispensing the liquid sample.

20 Claims, 7 Drawing Sheets

U.S. PATENT DOCUMENTS

| | | | |
|---|---|---|---|
| 5,985,214 A | 11/1999 | Stylli et al. ............. 422/65 |
| 6,001,309 A | 12/1999 | Gamble et al. | |
| 6,112,605 A | 9/2000 | Papen et al. ......... 73/864.22 |
| 6,326,212 B1 * | 12/2001 | Aoki ..................... 436/180 |
| 6,368,562 B1 * | 4/2002 | Yao ....................... 422/100 |
| 6,374,683 B1 * | 4/2002 | Hunicke-Smith et al. ................. 73/864.17 |
| 6,387,330 B1 * | 5/2002 | Bova et al. ............ 422/100 |
| 6,399,024 B1 * | 6/2002 | Bevirt et al. .......... 422/100 |
| 6,415,669 B1 * | 7/2002 | Carl ................... 73/864.14 |
| 6,474,180 B2 * | 11/2002 | Bigus ................. 73/864.11 |
| 6,517,778 B1 * | 2/2003 | Kumar et al. ....... 422/82.05 |
| 6,575,209 B2 * | 6/2003 | Gora ...................... 141/238 |
| 6,592,826 B1 * | 7/2003 | Bloecker et al. ...... 422/101 |
| 6,623,700 B1 * | 9/2003 | Horine et al. ......... 422/100 |
| 2002/0081747 A1 * | 6/2002 | Jacobs et al. .......... 436/174 |
| 2002/0176811 A1 * | 11/2002 | Peck et al. ............. 422/130 |

FOREIGN PATENT DOCUMENTS

| | | |
|---|---|---|
| EP | 0 545 284 A | 6/1993 |
| EP | 1 093 855 A | 4/2001 |
| EP | 1 101 532 A | 5/2001 |
| JP | 2002-202495 * | 7/2002 ............ B01J/4/02 |
| WO | WO99/09394 | 2/1999 |

OTHER PUBLICATIONS

Percin et al., Controlled ink–jet printing and deposition of organic polymers and solid particles, Applied Physics Letters 73(16):2375, 1998.

J.C. Yang, et al., A Simple Piezoelectric Droplet Generator; 23 Experiments in Fluids 445–447 (1997) (3 pages).

G. Percin, et al., Pizoelectrically Actuated Droplet Ejector, 68 REV. SCI. INSTRUM. 4561–4563 (Dec. 1997) (3 pages).

* cited by examiner

METHODS AND DEVICES FOR STORING AND DISPENSING LIQUIDS

RELATED APPLICATION

This application claims priority to U.S. Ser. No. 60/194,586, filed Apr. 5, 2000, which is incorporated herein by reference in its entirety.

BACKGROUND OF THE INVENTION

1. Field of the Present Invention

The present invention generally relates to devices and methods for storing and dispensing quantities of liquids. More specifically, the present invention uses a macro/micro interface and a micro electro mechanical system to store and dispense chemical and biological liquids in minute quantities.

2. Description of the Related Art

Until the relatively recent advent of combinatorial chemistry and genetic research spawned the need for high-throughput analyzing and screening techniques, researchers performed such assays using vials, tubes and beakers. However, with ever more substances available via synthesis or via combinatorial techniques for testing, the need has arisen to test the possible role of thousands, or even millions of substances, in comparable numbers of possible reactions. Miniaturization has been identified as a promising path to more efficient, e.g. less expensive, chemical, and in particular, drug, analysis and screening. Discussions of various aspects of such analysis and screening techniques are found in J. D. Devlin, ed., High Throughput Screening: The Discovery of Bioactive Substances (Marcel Dekker, Inc., New York, 1997); which is incorporated herein by reference to more fully describe the state of the art to which the present invention pertains.

A miniaturization apparatus may be broadly classified into at least two categories. A first category deals with microchemistry and involves the placement of chemical substances in small amounts in sites formed on glass or a similar substance. These small amounts generally range between picoliter and microliter aliquots. Such amounts shorten reaction times significantly over those conducted in reaction vessels holding on the order a fraction of a milliliter, as currently achievable by a lab technician working "by hand". In addition to microchemical testing, levels of gene expression and protein levels can be tested on a large scale using micro-chemistry.

An example of this first category is the development of microplate technology in which a substrate (e.g. plastic) may include site densities of up to about many thousand (e.g. 96 to about 10,000) sites. This technology generally includes the use of complex micro-robotics or the adaptation of ink-jet technology to apply chemical and biochemical substances to chosen sites on the substrates. Frequently, at least one of the reactants in a chemical assay to be performed is chemically linked to or otherwise immobilized at the reaction site, so that fluids may be added to and removed from the reaction site without removing an intermediate or end product of the reaction, since it is desirable that the intermediate or end product(s) is (are) to be retained at the reaction site, so that the outcome of the chemical assay may thereby be determined.

Currently, credit-card sized chips (e.g. glass chips) with greater than many thousand (e.g. 10,000) sites are in development (See Leach, 1997, Drug Discovery Today, 2:253). Each site may cover an area of 100 square microns and may contain much less than 1 microliter in volume. The chip is a glass sandwich formed from individual glass layers, which are glued together to form tubes to move substances between sites. The tubes are generally formed by cutting (e.g. etching), trenches or grooves in a first glass layer and then sandwiching the trenches under a second glass layer.

A second category of miniaturization apparatus (e.g. "lab on a chip") employs silicon or glass as some functional modality in some functional (e.g. electrical or mechanical) modality as a substrate, and chemicals then are tested on the substrate. This category of apparatus may include the use of electrokinetic motive forces. Micro-robotics or microchemistry, or both, may be employed with such substrates, including the use of micro-fluidic pumps (pumps having no moving parts) to move substances between sites, the use of electrophoresis or electrokinetic pressure pumping (a combination of electrophoresis and electro-osmosis) as motive agents to analyze chemical reactions acting over the surface of the silicon substrate (for about e.g. 25 reaction sites).

Currently, to achieve high-throughput analyzing and screening techniques for chemical and biochemical reactions, complex operations using combinations of films and substrates or complex robotics for the precise placement of fluids carrying chemical compositions, or both are required. Such complex systems are subject to failure due to their inherent complexity and are expensive to manufacture and maintain.

Moreover, current methods and systems for liquid sample processing consume large amounts of expensive, toxic and specialty reagents. This is especially true in the pharmaceutical arts when throughput rates for a singe lab can be up to 100,000 samples per day, where each sample includes a volume on the order of 2–20 microliters.

Accordingly, it is desirable to be able to process hundreds or thousands of liquid samples concurrently at a volume in the pico to micro liter range.

SUMMARY OF THE INVENTION

The devices and methods according to the present invention possess new capacities and capabilities in liquid handling, storage, and dispensing. The present invention enables the storing of liquid samples in any format (including a conventional 96 sample format) for a period of time, and also allows for the dispensing of the liquid samples in minute volumes. These volumes preferably range from picoliters to microliters.

Accordingly, the present invention provides a liquid handling device and method for storing and dispensing liquid samples in high density formats using liquid volumes with a range of several orders of magnitude.

The present invention also provides liquid handling devices and methods using a macro to micro interface and a new microelectro mechanical system for real-time re-arraying of combichem and biochemical libraries and other liquid samples, as well as a means for compound storage, compound indexing, and compound dispensing.

The liquid handling devices and methods according to the present invention is particularly suited for re-arraying combichem and biochemical libraries existing in 96 well formats into higher density formats, e.g. 384 or 1536 well formats. Higher density formats (e.g. 500,000, 1,000,000, and 2,000,000 samples) are within the scope of this invention.

Accordingly, in one aspect of the present invention, a liquid handling system includes a liquid handling substrate having a plurality of channels for conducting a liquid sample. The channels terminate in a corresponding plurality of exit ports in an outer surface of the substrate for transfer of a quantity of the liquid sample. The liquid handling system also includes a liquid storage and dispensing substrate having a plurality of cartridges corresponding to the channels, where the cartridges terminate in a corresponding plurality of exit ports in an outer surface of the substrate for transfer of a quantity of the liquid sample. Each channel includes a reservoir in communication with a corresponding cartridge which creates an interface between the channel and the cartridge. Each cartridge terminates at a dispensing device. The dispensing device may include a microelectro mechanical system (MEMS) comprising a membrane with an opening, a nozzle positioned adjacent to the opening on a side of the membrane and a piezoelectric element.

Liquid is conveyed in the present invention using any one or a combination of means including capillary action, pneumatic means, electroosmotic flow, and a minipump.

In another aspect of the present invention, the liquid handling system according to the above aspect may be used in a method having the steps of drawing a liquid sample into the channels either by capillary action, pneumatic means, electroosmotic flow, a minipump or any combination thereof, storing the liquid sample in the cartridges, and dispensing the liquid sample after a period of time.

Moreover, the above aspect may include further features including:

- a liquid detecting means comprising a light emitting diode (LED) and a photo-detector, for detecting a level of a liquid sample in a cartridge;
- a monolithic assembly of all cartridges;
- separable cartridges, which may be separated using a multifunctional head arrayed in either a fountain, roller, conveyor belt or chain geometry;
- electrical conductor(s) for supplying electrical energy to the liquid detecting means and the liquid storage and dispensing substrate; and
- a registration mark and/or indexing mark on the outer surface of the cartridge.

For a better understanding of the invention, reference is made to the below referenced drawings and written description following immediately thereafter.

DETAILED DESCRIPTION OF THE INVENTION

Figure 1D:
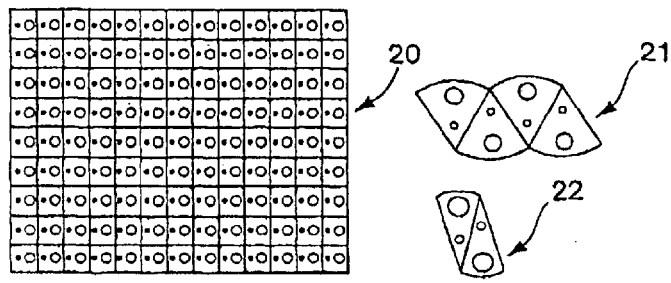
FIGS. 1A–1D are schematic diagrams of one embodiment of the liquid handling system.
Figure 1C:
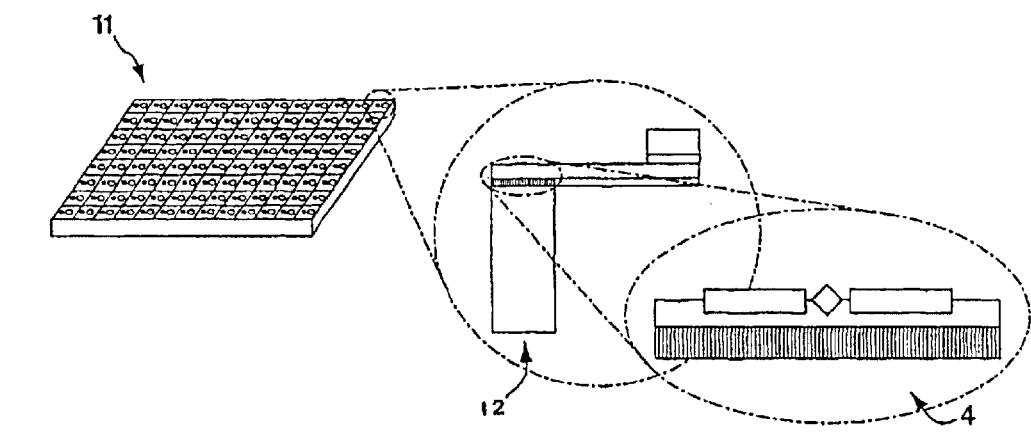
Figure 1A:
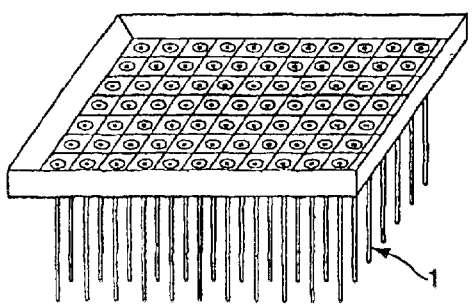
Figure 1B:
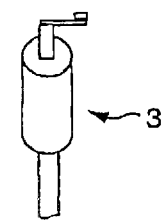

As shown in FIGS. 1A–1D, a macro interface includes 96 glass (or other comparable material) capillary tubes 1 arrayed in a conventional 96 sample format, fixed in place relative to one another. A corresponding micro interface 11 includes 96 cartridges 12 fixed in place relative to one another by a holder. A liquid sample reservoir 3 is positioned between each capillary tube and corresponding cartridge. The array may be arranged in any number of arrangements for yielding the desired number of tubes and cartridges. Such arrangements are illustrated in FIG. 1D 20–22.

Figure 2A:
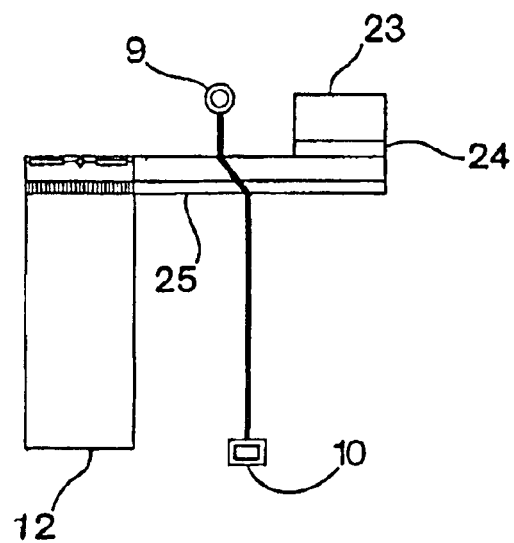
FIGS. 2A–2B are schematic diagrams of one embodiment of the cartridge of the liquid storage and dispensing substrate and the MEMS.
Figure 2B:
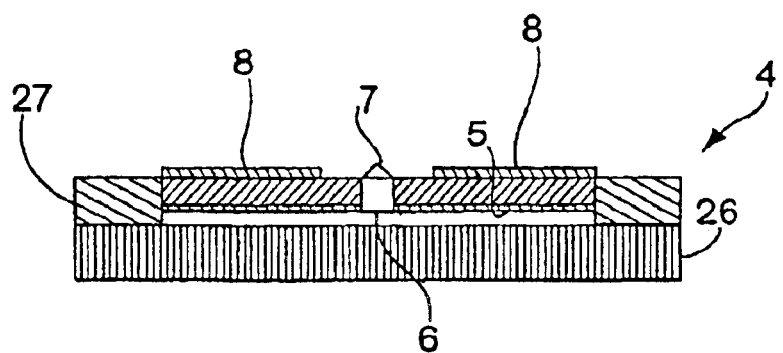
Figure 3:
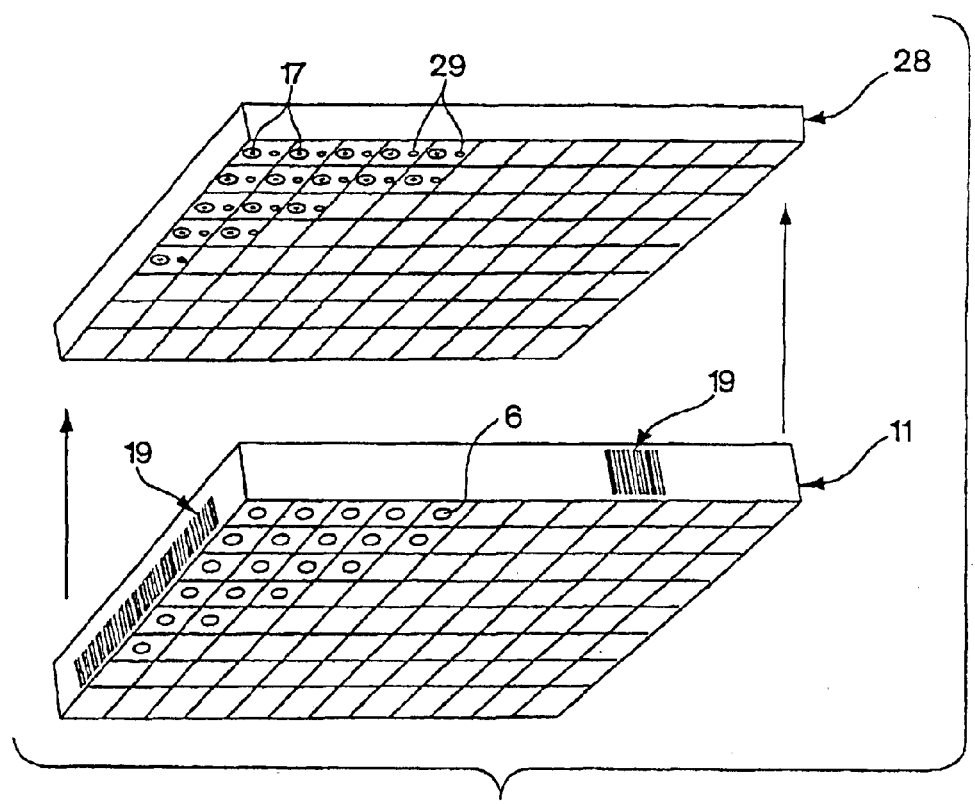
FIG. 3 is a schematic diagram of one embodiment of the liquid storage and dispensing substrate in which the cartridges are arranged in a monolithic array.

FIGS. 2A–B, illustrate enlarged views of a cartridge 12 and a micro-electrical, mechanical system (MEMS) 4 positioned on one end of the cartridge. A liquid sample flows from the liquid handling substrate through the reservoir into a lower part of the cartridge. Applying a vacuum to orifice 23 forces liquid to enter the cartridge to "prime" the cartridge. Once the cartridge is primed, the liquid storage and dispensing substrate is inverted and both sides of the cartridge are sealed with an appropriate sealant to prevent evaporation, cross-contamination of the sample, and the introduction of particulate matter therein. A hydrophobic membrane 24 positioned adjacent the orifice 23 allows airflow into and out of the cartridge and prevents the liquid sample from being drawn out of the cartridge at the orifice 23.

A liquid sensing system monitors the liquid sample level in the cartridge. Using an LED 9, collimated light is sent through a narrow bleed passageway 25 that separates the MEMS 4 from the vacuum orifice 23. When a liquid sample is present, light is refracted to a photodetector 10 positioned on an opposite side of the bleed passageway 25 from the LED 9. Light is refracted away from the photodetector 10, however, when the level of the liquid sample becomes too low after dispensing of the liquid sample or if the device loses its prime and the bleed passageway 25 does not contain liquid.

Fluid flows from the lower part of the cartridge through a micro-filter 26 (for removing particulate matter) as shown in FIG. 2B, so that clogging of a silicon nozzle 7 at an exit orifice 6 is avoided. The exit orifice 6 is defined by a region surrounded by a silicon membrane 5, which is held in place by a glass substrate 27. The exit orifice and silicon nozzle are created by micro-etching the silicon membrane. Coating the silicon membrane is a piezoelectric substance 8 that acts as an actuator for dispensing fluid. To dispense a fluid, the silicon nozzle points in a downward direction and electrical energy is supplied to the piezoelectric substance. This causes the silicon membrane to flex and results in droplet ejection from the nozzle.

During assaying of the liquid sample, individual cartridges 12 may be separated from other cartridges of the liquid storage and dispensing substrate. However, it is also possible to maintain the cartridges in the same positions relative to one another creating a monolithic dispenser 11. Accordingly, each cartridge includes registration 18 and indexing marks 19 on the surface of the cartridges so that the cartridge may be easily aligned and identified when the cartridges are separated from one another. The cartridges are then fed in a serial manner into a multifunctional head reader 28.

The multifunctional head reader 28 includes an array of elements having electrical conductors 17 for supplying electrical energy to the cartridge 12 and an array of detectors 29 for determining the chemistry of the dispensed liquid samples. The head device may be designed in any number of geometries as indicated in the examples set forth below.

EXAMPLE 1
Multifunctional Head Device in a Fountain Geometry

Figure 4:
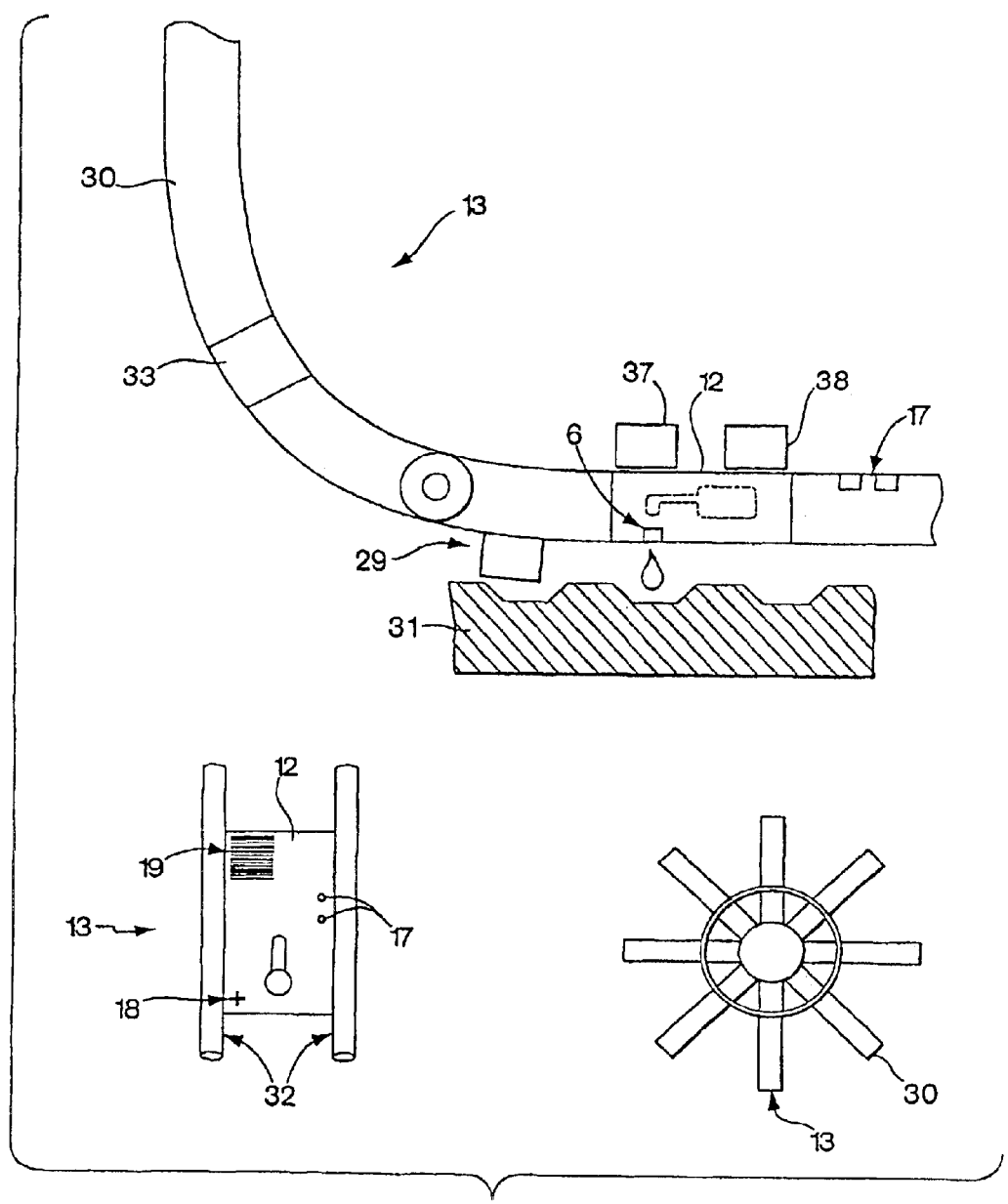
FIG. 4 is a schematic diagram of one embodiment of the liquid storage and dispensing substrate in which the separable cartridge are arranged in a fountain geometry.

As shown in FIG. 4, a fountain geometry 13 of individual cartridges 12 are fed down through a set of tracks 31 arrayed across the assay substrate 31. in a spoke-like manner. Each of the tracks may house two belts 32 on either side of a horizontal portion of the track. Cartridges are drawn into the horizontal portion of the track via gravity and then conducted across the surface of the substrate by the two belts on either side. The bottom and tops of the tracks may include air bearings or a material 33 with a low coefficient of friction 33 to ease passage of the cartridges through the tracks. The tracks may also contain electrical conductors 17 that may run the length of the horizontal portion of the track or are split into discrete contact points. To dispense liquid, electrical energy is supplied to the electrical conductors 17 at an appropriate time when the cartridge 12 is positioned over a target. To ensure accurate positioning of the particular cartridge, the tracks may include one or more sensors 37 to detect registration marks 18 and one or more sensors 38 to detect indexing marks 19 provided on the cartridges. Sensors for chemistry detection 29 may also be used and may be positioned on the underside of the tracks or placed on rails between the tracks.

EXAMPLE 2
Multifunctional Head Device in a Roller Geometry

Figure 5:
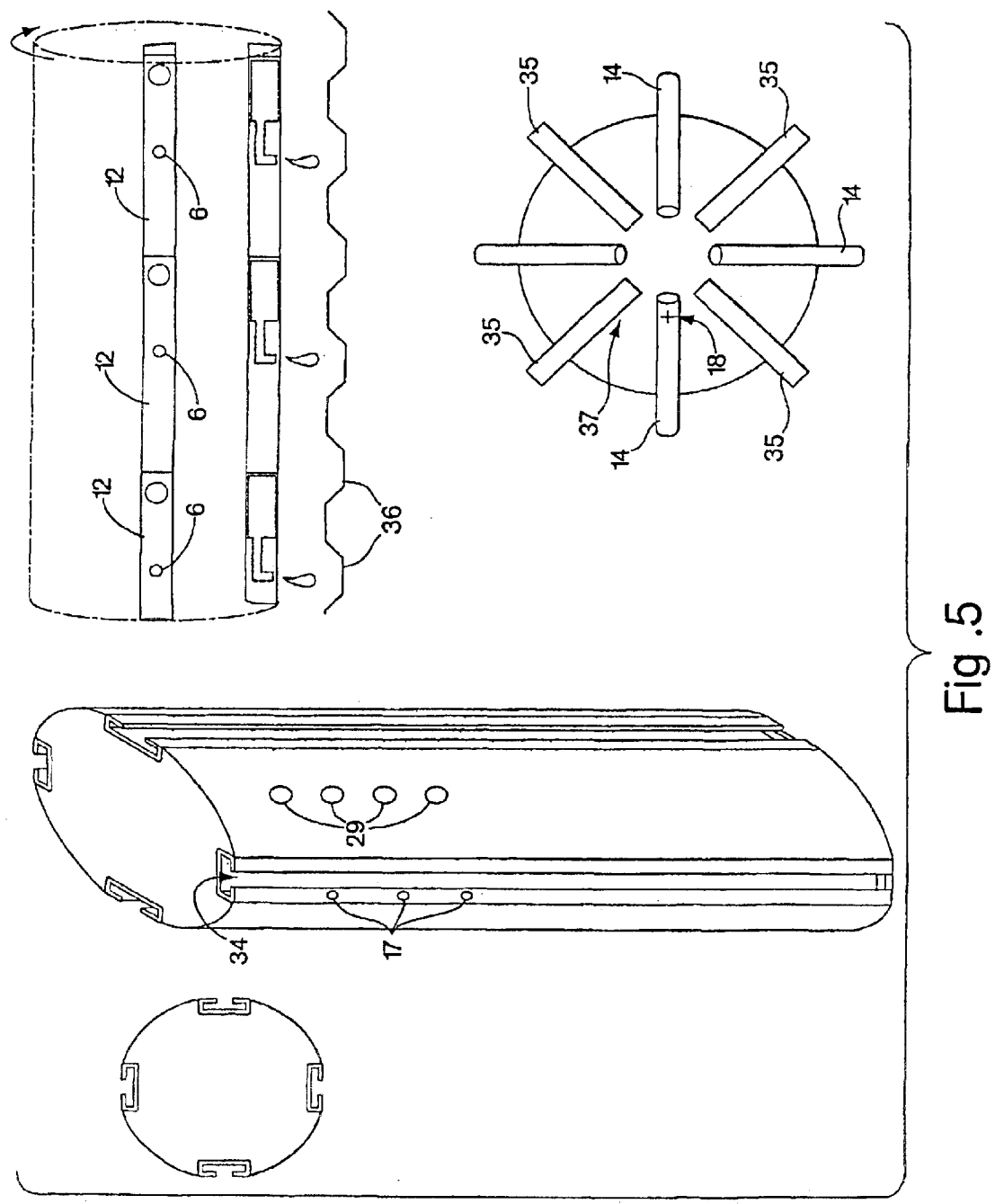
FIG. 5 is a schematic diagram of one embodiment of the liquid storage and dispensing substrate in which the separable cartridges are arranged in a roller geometry.

As shown in FIG. 5, roller geometry tracks 34 similar to those described in Example 1 are arrayed in a cylindrical manner. Cartridges 12 are positioned into the tracks 34 with the exit orifice 6 of each dispenser facing outwards. Each track includes a row of cartridges which may be staggered relative to one another at a pitch corresponding to reaction sites below or some multiple of the pitch. The cartridges may be locked into each track via a pressure plate applied to the open end to ensure that each cartridge is snuggly positioned adjacent cartridges. This insures proper alignment of the cartridges within the track. Either contiguous or discrete electrical conductors 17 or a combination of the two may be placed along the length of each track to provide electrical energy to dispense liquid from an entire row of cartridges, individual cartridges in the row, or groups of cartridges within a row. Registration marks 18 on the cartridges may also be read via a detector 37 to ensure proper registration of the cartridges with respect to the roller 14 and chemistry substrate 36. Dispensing is accomplished by rotating the roller 14 so that the appropriate track 34/cartridge 12 is positioned over the reaction sites 36 and then energized via the electrical conductors 17. Sensors 29 to detect chemical activity may also be used and positioned between the tracks, in another roller (a detection roller 35) or may be part of an overhanging arm positioned adjacent to the dispenser roller arm. In order to increase throughput, multiple rollers may also be used.

EXAMPLE 3
Multifunctional Head Device in a Conveyor Belt Geometry

Figure 6:
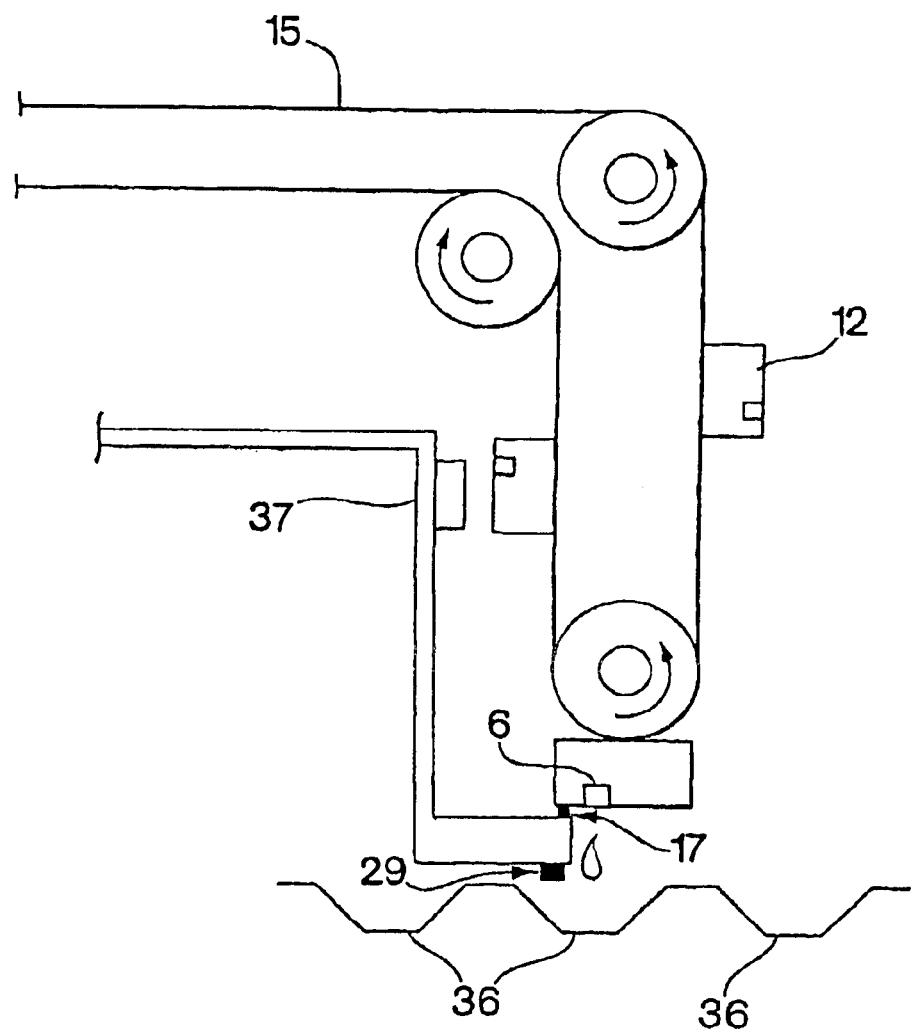
FIG. 6 is a schematic diagram of one embodiment of the liquid storage and dispensing substrate in which the separable cartridges are arranged in a conveyor belt geometry.

As shown in FIG. 6, in the conveyor belt 15 geometry individual cartridges 12 are affixed to a conveyor belt 15 that transports each cartridge 12 to its appropriate dispensing location. At the point of alignment where the cartridge is horizontal, electrical conductors 17 are in place to transmit electrical energy to actuate the dispenser. Additionally a sensor 37 may be placed adjacent to this point to ensure accurate registration of the dispenser with respect to the reaction site 36 below. A sensor 29 to detect chemical activity may also be placed at this location.

EXAMPLE 4
Multifunctional Head Device in a Chain Geometry

Figure 7:
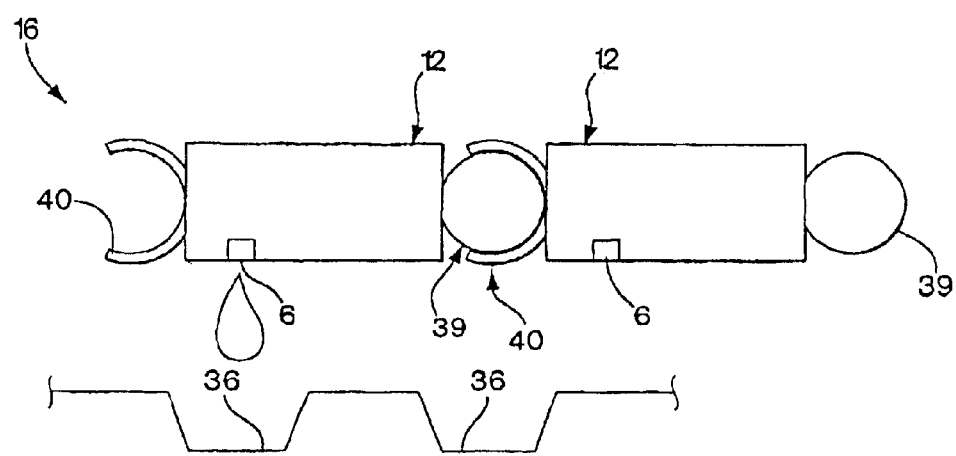
FIG. 7 is a schematic diagram of one embodiment of the liquid storage and dispensing substrate in which the separable cartridges are arranged in a chain geometry.

As shown in FIG. 7, in the chain geometry 16 individual cartridges 12 are linked male end 39 to female end 40 in a manner similar to that of a bicycle chain. In essence the linked cartridges form a conveyor belt similar to that seen in Example 3, supra. By either using a sprocket and teeth system or a friction drive system the cartridges can be aligned with respect to the reaction sites using a similar geometry and instrumentation to that described supra in Example 3.

Having thus presented the present invention in view of the above described embodiments, various alterations, modifications and improvements will readily occur to those skilled in the art. Such alterations, modifications and improvements are intended to be within the scope and spirit of the invention. Accordingly, the foregoing description is by way of example only and is not intended to be limiting. The invention's limit is defined only in the following claims and the equivalents thereto.

What is claimed is:

1. A liquid handling system, comprising:
   a liquid handling substrate having a plurality of channels for conducting a liquid sample, said channels terminating in a plurality of exit ports in an outer surface of said substrate for transfer of a quantity of said liquid sample; and
   a liquid storage and dispensing substrate having a plurality of cartridges corresponding to said channels, said cartridges terminating in a plurality of exit ports in an outer surface of said substrate for transfer of a quantity of said liquid sample, wherein
   each said channel includes a reservoir in communication with a corresponding cartridge creating an interface therebetween, and wherein
   each said cartridge terminates at a dispensing device,
   and wherein said dispensing device comprises a micro-electro mechanical system (MEMS) comprising a membrane with a hole, a nozzle positioned adjacent to said hole on a side of said membrane and a piezoelectric element.

2. The liquid handling system of claim 1, wherein a liquid sample enters said channels of said liquid handling substrate by either capillary action, pneumatic means, electroosmotic flow, a minipump or a combination thereof.

3. The liquid handling system of claim 1, further comprising a liquid detecting means for detecting a level of a liquid sample in a cartridge.

4. The liquid handling system of claim 3, wherein said liquid detecting means comprises a light emitting diode and a photo-detector.

5. A liquid handling system, comprising:
   a liquid handling substrate having a plurality of channels for conducting a liquid sample, said channels terminating in a plurality of exit ports in an outer surface of said substrate for transfer of a quantity of said liquid sample; and
   a liquid storage and dispensing substrate having a plurality of cartridges corresponding to said channels, said cartridges terminating in a plurality of exit ports in an outer surface of said substrate for transfer of a quantity of said liquid sample, wherein
   each said channel includes a reservoir in communication with a corresponding cartridge creating an interface therebetween, a liquid detecting means, and wherein each said cartridge terminates at a dispensing device, and wherein said cartridges are separable, and wherein said cartridges include an electrical conductor for supplying electrical energy to a liquid detecting means and said liquid storage and dispensing substrate.

6. The liquid handling system of claim 5, wherein each said separable cartridge includes a registration mark on the outer surface of said cartridge.

7. The liquid handling system of claim 5, wherein each said separable cartridge includes an indexing mark on the outer surface of said cartridge.

8. The liquid handling system of claim 5, wherein each said separable cartridge includes a registration mark and an indexing mark on the outer surface of said cartridge.

9. A liquid handling system, comprising:

a liquid handling substrate having a plurality of channels for conducting a liquid sample, said channels terminating in a plurality of exit ports in an outer surface of said substrate for transfer of a quantity of said liquid sample; and a liquid storage and dispensing substrate having a plurality of cartridges corresponding to said channels, said cartridges terminating in a plurality of exit ports in an outer surface of said substrate for transfer of a quantity of said liquid sample, wherein each said channel includes a reservoir in communication with a corresponding cartridge creating an interface therebetween, a multifunctional head, and wherein each said cartridge terminates at a dispensing device, and wherein said cartridges are separable using said multifunctional head, said head arrayed in a fountain, roller, conveyor belt or chain geometry, and wherein said cartridges are readable by said multifunctional head.

10. The liquid handling system of claim 9, wherein said dispensing device comprises a microelectro mechanical system (MEMS) comprising a membrane with a hole, a nozzle positioned adjacent to said hole on a side of said membrane and a piezoelectric element.

11. The liquid handling system of claim 9, wherein the plurality of channels number up to approximately 1536.

12. The liquid handling system of claim 9, wherein each said separable cartridge includes a registration mark on the outer surface of said cartridge.

13. A liquid handling system, comprising:

a liquid handling substrate having a plurality of channels for conducting a liquid sample in said substrate, said channels terminating in a plurality of exit ports in an outer surface of said substrate for transfer of a quantity of said liquid sample;

a liquid storage and dispensing substrate having a plurality of separable cartridges corresponding to said channels, said cartridges terminating in a plurality of exit ports in an outer surface of said substrate for transfer of a quantity of said liquid sample;

a liquid detecting system comprising a light emitting diode and a photo-detector, wherein each said channel includes a reservoir in communication with a corresponding cartridge creating an interface therebetween, and wherein said liquid sample enters said channels either by capillary action, pneumatic means, electro-osmotic flow, a minipump or a combination thereof.

14. The liquid handling system of claim 13, wherein the plurality of channels number up to approximately 1536.

15. The liquid handling system of claim 13, wherein each said separable cartridge includes a registration mark on the outer surface of said cartridge.

16. The liquid handling system of claim 13, wherein each said separable cartridge includes an indexing mark on the outer surface of said cartridge.

17. In a liquid handling system, comprising:

a liquid handling substrate having a plurality of channels for conducting a liquid sample in said substrate, said channels terminating in a plurality of exit ports in an outer surface of said substrate for transfer of a quantity of said liquid sample;

a liquid storage and dispensing substrate having a plurality of separable cartridges corresponding to said channels, each said cartridge terminating at a microelectro mechanical system (MEMS) comprising a laminate of glass, silicon and a piezoelectric substance; and a liquid detecting system comprising a light emitting diode and a photo-detector, wherein each said channel includes a reservoir in communication with a corresponding cartridge creating an interface therebetween, and wherein said liquid sample enters said channels wither by capillary action, pneumatic means, electroosmotic flow, a minipump or a combination thereof, a method for storing and dispensing liquids, comprising:

drawing a liquid sample into said channels either by capillary action, vacuum, electroosmotic flow, a minipump or any combination thereof;

storing said liquid sample into said cartridges; and dispensing said liquid sample.

18. The liquid handling system of claim 17, wherein the plurality of channels number approximately 96, 384 or 1536.

19. The liquid handling system of claim 17, wherein each said separable cartridge includes a registration mark on the outer surface of said cartridge.

20. The liquid handling system of claim 17, wherein each said separable cartridge includes an indexing mark on the outer surface of said cartridge.

* * * * *

UNITED STATES PATENT AND TRADEMARK OFFICE
CERTIFICATE OF CORRECTION

PATENT NO. : 6,905,657 B2
DATED : June 14, 2005
INVENTOR(S) : Allyn Hubbard et al.

It is certified that error appears in the above-identified patent and that said Letters Patent is hereby corrected as shown below:

Column 8,
Line 22, delete the word "In" and insert -- A method for storing and
dispensing liquids comprising:
    providing --.
Lines 46, 48 and 51, delete the words "The liquid handling system" and insert -- The method --.

Signed and Sealed this

Fourth Day of October, 2005

JON W. DUDAS
*Director of the United States Patent and Trademark Office*